(12) United States Patent
Meier

(10) Patent No.: US 6,685,807 B2
(45) Date of Patent: Feb. 3, 2004

(54) MEASURING PROBE FOR POTENTIOMETRIC MEASUREMENTS, METHOD OF MONITORING THE STATE OF AGING OF THE MEASURING PROBE, AND USE OF THE MEASURING PROBE

(75) Inventor: Peter C. Meier, Wohlen (CH)

(73) Assignee: Mettler-Toledo GmbH, Greifensee (CH)

(*) Notice: Subject to any disclaimer, the term of this patent is extended or adjusted under 35 U.S.C. 154(b) by 53 days.

(21) Appl. No.: 09/912,013

(22) Filed: Jul. 24, 2001

(65) Prior Publication Data

US 2002/0011422 A1 Jan. 31, 2002

(30) Foreign Application Priority Data

Jul. 25, 2000 (DE) .......................... 100 36 039

(51) Int. Cl.[7] .............................. G01N 27/26
(52) U.S. Cl. ................. 204/401; 204/400; 204/435
(58) Field of Search .................. 204/400, 415, 204/401, 431, 432, 435; 205/782.5, 783

(56) References Cited

U.S. PATENT DOCUMENTS

| | | | | |
|---|---|---|---|---|
| 2,752,308 | A | * | 6/1956 | Andrus |
| 3,132,082 | A | * | 5/1964 | Overmyer |
| 4,608,148 | A | | 8/1986 | Frollini, Jr. et al. |
| 4,686,011 | A | * | 8/1987 | Jackle |
| 4,959,138 | A | * | 9/1990 | Brinkmann et al. |
| 5,215,644 | A | * | 6/1993 | Ashikaga |
| 5,326,447 | A | * | 7/1994 | Fletcher |
| 5,445,726 | A | | 8/1995 | Cammann |

FOREIGN PATENT DOCUMENTS

| | | |
|---|---|---|
| DE | 3228647 | 2/1984 |
| DE | 3405431 | 11/1987 |
| DE | 3818846 | 12/1988 |
| DE | 195 33 059 C2 | 10/1999 |

* cited by examiner

Primary Examiner—T. Tung
(74) Attorney, Agent, or Firm—Friedrich Kueffner

(57) ABSTRACT

A measuring probe for potentiometric measurements has a housing (2) of an electrically insulating material surrounding an enclosed space (4). Inside the space (4) are a primary reference element (6), a secondary reference element (8), an electrolyte (10), and an ion-permeable, micro-porous, high-viscosity polymer substance which, in combination with the electrolyte (10), forms a filler mass (16). The housing (2) has at least one opening (12) to the outside, through which the electrolyte (10) can be brought into contact with a sample solution on which a measurement is to be performed. The secondary reference element (8) is arranged so that the boundary (52) of an electrolyte-deficient region (54) advancing over time from the opening (12) towards the primary reference element (6) arrives at the secondary reference element (8) before reaching the primary reference element (6).

22 Claims, 1 Drawing Sheet

MEASURING PROBE FOR POTENTIOMETRIC MEASUREMENTS, METHOD OF MONITORING THE STATE OF AGING OF THE MEASURING PROBE, AND USE OF THE MEASURING PROBE

BACKGROUND OF THE INVENTION

The present invention relates to a measuring probe for potentiometric measurements. The probe has a housing of an electrically insulating material surrounding an enclosed space that contains a primary reference element and an electrolyte. The housing has at least one opening through which the electrolyte can be brought into contact with a sample solution on which a measurement is to be performed. The enclosed space is filled with an ion-permeable, micro-porous, high-viscosity polymer substance which, in combination with the electrolyte, forms a filler mass of the measuring probe. The invention also relates to a method of monitoring the state of aging of the measuring probe, and it further relates to the use of the measuring probe for applications in process monitoring and process control.

A widely used kind of measuring probe for potentiometric measurements of ion concentrations or redox potentials is equipped with a diaphragm of porous material. The diaphragm serves to bring a reference—and/or bridge electrolyte, normally in the form of a liquid contained inside the measuring probe, into contact with a test solution. Particularly in chemical or micro-biological process-monitoring and process-control applications, the diaphragm may be subject to contamination which can falsify the results of the measurements.

Another measuring probe, known from DE 34 05 431 C2, belongs to the same general category of measuring probes but does not have a diaphragm and is significantly less prone to contamination. It has a housing of an electrically insulating material with at least one enclosed space containing a reference element and an electrolyte. The housing has at least one opening through which the electrolyte can be brought into contact with the test medium on the outside of the housing, i.e., a liquid solution on which a measurement is to be performed. The enclosed space inside the housing is filled with an ion-permeable, micro-porous, high-viscosity polymer substance which, in combination with the electrolyte, forms a filler mass of the measuring probe. This type of construction assures that the electrical potential measured at the reference element is highly constant even if the solutions being measured are strongly contaminated. In addition, the measuring probe can sustain pressure levels significantly in excess of 10 bar.

Measuring probes of the foregoing description are known to have the problem that as the cumulative operating time of the probe advances, the electrolyte that is initially contained in the polymer substance will to an increasing degree migrate into the test solution, resulting in a progressively spreading electrolyte deficiency in the polymer substance inside the housing. The increasing electrolyte deficiency in the polymer substance is also referred to as the aging process of the measuring probe and produces the undesirable effect that, when the electrolyte deficiency eventually reaches the reference element, there will be a change in the electrical potential measured at the reference element. To avoid the risk of erroneous measuring results, it is therefore necessary to monitor the aging process of the measuring probe. In particular, it should be possible to detect sufficiently in advance, i.e., with an adequate pre-warning interval, when the electrolyte deficiency is approaching the reference element.

According to DE 34 05 431 C2, the problem of detecting the advancement of the electrolyte deficiency can be solved by using an electrolyte consisting of a suspension of homogeneously distributed particles of a neutral salt with ions of equal transport number in an aqueous solution of the neutral salt. The polymer substance and the neutral salt suspension together form a gel that has a turbid appearance due to the salt particles in suspension. The state of aging of the measuring probe can be visually detected, as the turbidity disappears progressively with the advancement of the aging process. The reason for the decrease in turbidity is that the suspended neutral salt particles continuously pass into solution until a final state has been reached where there are essentially no suspended particles left and, as a result, the turbidity is strongly diminished. It has been found that in the aging process, a clearly visible boundary develops between a turbid portion of the gel where the neutral salt particles are homogeneously suspended and a comparatively clear portion where the neutral salt particles have passed into solution. As the boundary advances over time from the opening in the housing towards the reference element, the state as well as the speed of aging of the measuring probe can be determined from a visual observation of the boundary in the polymer gel.

However, the measuring probe according to DE 34 05 431 C2 has several drawbacks. To monitor the state of aging, it is necessary to be able to clearly see inside the enclosed space of the measuring probe. This precludes the use of a non-transparent material for the housing, and it also presents a problem with a transparent housing if the latter becomes contaminated by surface deposits. A further severe problem occurs if the gel in the enclosed space becomes discolored or contaminated, e.g., by the infusion of colored substances or infiltration of dirt particles from the test solution, which could make it practically impossible to visually detect the boundary of the electrolyte deficiency. It also has to be counted as a drawback that the electrolyte needs to be a suspension of homogeneously distributed particles of a neutral salt with ions of equal transport number in an aqueous solution of the neutral salt, a condition that excludes other kinds of electrolytes from being used in the measuring probe.

OBJECT OF THE INVENTION

A first object of the present invention is to provide an improved measuring probe that is free of the aforementioned drawbacks. A further object of the invention is to provide a method of monitoring the state of aging of a measuring probe, and a third object is to propose a use of the improved measuring probe.

SUMMARY OF THE INVENTION

A measuring probe according to the present invention has a housing of an electrically insulating material surrounding an enclosed space that contains a primary reference element and an electrolyte. The housing has at least one opening through which the electrolyte can be brought into contact with the outside of the housing, i.e., with a sample solution on which a measurement is to be performed. The enclosed space is filled with an ion-permeable, micro-porous, high-viscosity polymer substance which, in combination with the electrolyte, forms a filler mass of the measuring probe. The measuring probe of the present invention has a secondary reference element contained inside the enclosed space and arranged in such a manner that an electrolyte deficiency advancing from the opening towards the primary reference element arrives at the secondary reference element before it reaches the primary reference element.

In the measuring probe according to the foregoing description, the state of aging is monitored by using a method that is likewise part of the present invention, with the steps of a) detecting continually or at intervals the difference $(V_1-V_2)$ between the respective electrical potentials $V_1$ and $V_2$ of the primary and secondary reference element, and b) generating a signal when the difference between the potentials exceeds a previously specified threshold value, and/or if the difference between the potentials changes at a rate that exceeds a previously specified threshold rate.

The invention also encompasses the use of the inventive measuring probe in process-monitoring and process-control applications.

With the inventive concept of arranging a secondary reference element in the enclosed space of the measuring probe so that an electrolyte deficiency advancing from the opening towards the primary reference element reaches the secondary reference element before it arrives at the primary reference element, it is no longer necessary to visually inspect the enclosed space in order to determine the state of aging of the measuring probe. In particular, a measuring probe according to the invention can have a non-transparent housing, or it can be a built-in part of an apparatus. In addition, the state of aging can also be monitored if the housing is covered with contaminants, as may be the case if the measuring probe is used for dirty or foamy sample solutions. Furthermore, a measuring probe according to the present invention does not require the special kind of electrolyte that is needed with the state-of-the-art probe described above in order to make the boundary of the electrolyte deficiency visible. Thus, there is a wider choice of electrolytes available to be used in combination with the polymer substance, without the previous limitation to a suspension of homogeneously distributed particles of a neutral salt with ions of equal transport number in an aqueous solution of the neutral salt. In particular, a measuring probe of the present invention can work with an electrolyte consisting of a saturated or near-saturated solution of a neutral salt in an appropriate solvent, e.g., a near-saturated solution of potassium chloride in water.

With the inventive method of continuously or intermittently monitoring the difference between the electrical potentials of a primary reference element and a secondary reference element against a threshold value or a threshold rate of change, the state of aging of the measuring probe can be reliably ascertained. In particular, the invention provides a convenient way of automating the monitoring function. Thus, the inventive measuring probe can be used advantageously for applications in process monitoring and process control.

In a preferred embodiment of the invention, the primary reference element is configured as a primary cartridge containing a primary electrode and a primary electrolyte. The required electrical contact between the primary electrolyte and the electrolyte in the enclosed space inside the housing of the probe can be established in a known manner through a diffusion zone of, e.g., fiberglass wool or cotton. Alternatively, the primary cartridge may have a primary passage opening. The choice of the primary electrolyte generally depends on the design of the primary electrode, but also on the composition and properties of the electrolyte in the enclosed space. In one embodiment of the invention, the primary electrolyte is mixed with the same polymer substance that is also used in the filler mass.

In advantageous embodiments of the invention, the secondary reference element is configured as a secondary cartridge containing a secondary electrode and a secondary electrolyte. Analogous to the primary cartridge, the secondary cartridge can have a secondary passage opening, and the secondary electrolyte can be provided in a mixture with the same polymer substance that is also used in the filler mass.

In an advantageous embodiment of the invention, one end of the secondary electrode is immersed in the primary electrolyte. In another embodiment, one end of the secondary electrode is immersed in the electrolyte in the enclosed space of the measuring probe in an area outside the primary cartridge. These two arrangements of the secondary electrode have the advantage that they lengthen the distance along which the boundary of the electrolyte deficiency advances from the probe opening to the primary reference element, so that the measuring probe lasts longer before it reaches the end of the aging process.

The primary electrode and/or the secondary electrode can be configured as wire electrodes of a known design, e.g., in the form of a silver wire, one end of which is coated with silver chloride and immersed in the electrolyte of the respective electrode. Alternatively, at least one of the reference elements may have an electrode in the form of a conductive track deposited, e.g., on the inner or outer wall surface of a reference element cartridge or on the inner wall surface of the measuring probe housing.

In a particularly preferred embodiment of the invention, the electrolyte in the enclosed space of the measuring probe housing is a suspension of homogeneously distributed particles of a neutral salt with ions of equal transport number in an aqueous solution of the neutral salt. This has the advantage that the entire filler mass contains a considerable supply of electrolyte, which works to the advantage of a long operating period of the measuring probe. Potassium chloride has proven to be a particularly advantageous choice for the neutral salt. Preferred is a suspension of fine particles of potassium chloride in an aqueous or part-aqueous potassium chloride solution. The proportion of suspended potassium chloride should be at least 30% and may be as high as 1500% in relation to the dry weight of the polymer substance. A preferred range is between 100% and 800%, and the highest preference is for 200% to 400%.

According to a further embodiment of the invention, the measuring probe is configured as a reference electrode, so that the measuring probe can be used as a reference element, e.g., for a pH electrode or another measuring electrode. In another preferred embodiment of the invention, the measuring probe is configured as a single-rod measuring chain, which has the advantages that it is compact and simple to operate.

A preferred measuring probe according to the invention is also equipped with a means for monitoring the difference between the respective electrical potentials of the primary and secondary reference element. This makes the measuring probe particularly suitable for applications in process monitoring and/or process control.

DETAILED DESCRIPTION OF THE INVENTION

Figure 1:
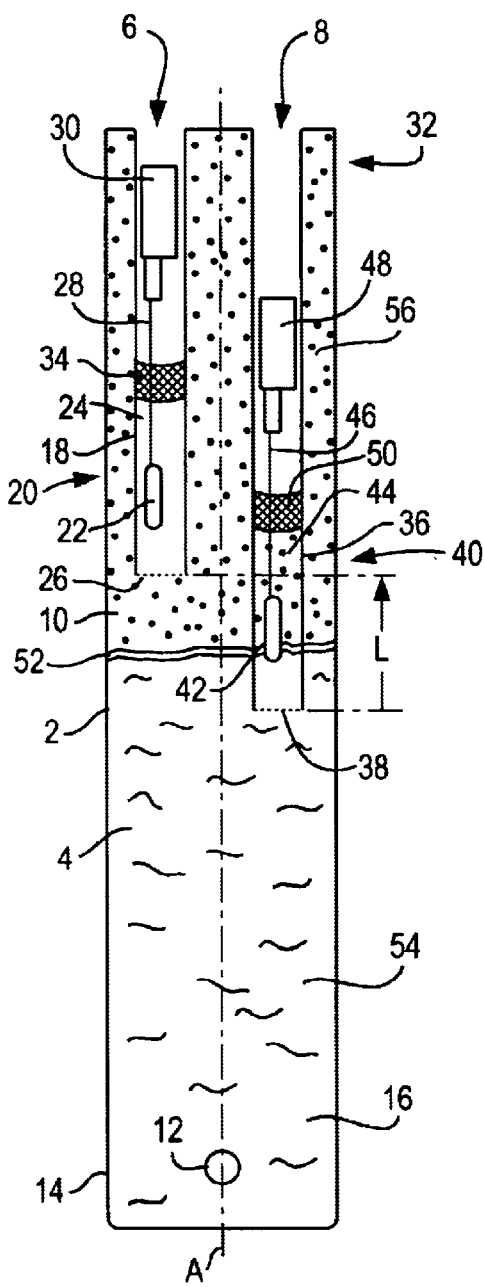
FIG. 1 represents a lengthwise section of a measuring probe that is configured as a reference electrode.

FIG. 1 illustrates a measuring probe configured as a reference electrode with a tubular housing 2, usually referred to as the electrode shaft and consisting of an electrically insulating material, e.g., glass or a polymer material such as a polyarylether ketone (PAEK), in particular a polyetherether ketone (PEEK). The housing 2 surrounds an enclosed space 4 containing a primary reference element 6, a secondary reference element 8, as well as an electrolyte 10. The housing 2 has an opening 12, so that when the measuring probe is dipped into a sample solution (not shown), the electrolyte 10 is brought into contact with the sample solution. In the illustrated example, the opening 12 is formed as a passage hole in an end portion 14 of the housing 2. The enclosed space 4 is filled with an ion-permeable, high-viscosity, micro-porous polymer material which, in combination with the electrolyte 10, forms a filler mass 16. To prevent the filler mass 16 from running out of the housing through the opening 12, the filler mass should be in a highly viscous or even solid state at the normal operating temperature range of the measuring probe. As a polymer filler mass to meet this criterion, a copolymer of acrylamide and N,N$^1$-methylene-bis-acrylamide has been tried and proven.

The primary reference element 6 is configured as a cartridge 18 that is open on one side and contains a primary electrode 20 of a known potential. For example, the primary electrode is configured as an Ag/AgCl electrode with a chlorided silver wire 22 that is immersed in a primary electrolyte 24. To prevent the primary electrolyte 24 from running out of the open end 26 of the cartridge 18, the primary electrolyte 24 is enclosed in the pores of an ion-permeable, micro-porous polymer substance, preferably the same material as in the filler mass 16. On the far side from the open end 26, the primary reference element 6 has a plug-in contact 30 that communicates with the primary electrode 20 through a conductor lead 28, e.g., a platinum wire. The plug-in contact 30 serves to establish a connection to circuit elements contained in the header 32 of the measuring probe or outside of the housing. In addition, the primary reference element 6 contains a sealing plug 34, e.g., of glass or a polymer material, to prevent the plug-in contact 30 from touching the primary electrolyte 24. Instead of the axially facing opening 26, the primary reference element 6 could have a lateral opening if desired.

The measuring probe illustrated in FIG. 1 as an example of the invention has a secondary reference element 8 that is essentially identical to the primary reference element 6. Thus, the secondary reference element 8 has a cartridge 36 with an open end 38 and a secondary electrode 40 configured as an Ag/AgCl electrode with a chlorided silver wire that is immersed in a secondary electrolyte 44. The secondary electrolyte 44 is enclosed in the pores of an ion-permeable, micro-porous polymer substance, preferably the same polymer material as in the filler mass 16. In addition, the secondary reference element 8 has a plug-in contact 48 that communicates with the secondary electrode 40 through a conductor 46, e.g., a platinum wire. The plug-in contact 48 serves to establish a connection to circuit elements contained in the header 32 of the measuring probe or outside of the housing 2. In addition, the secondary reference element 8 contains a sealing plug 50, e.g., of glass or a polymer material, to prevent the plug-in contact 48 from touching the secondary electrolyte 44.

As may be seen in FIG. 1, the primary reference element 6 and the secondary reference element 8 are positioned in the measuring probe at parallel but staggered positions, with the open end 26 of the primary reference element 6 being farther removed from the opening 12 than the open end 38 of the secondary reference element 8. As will be discussed below in further detail, the staggered arrangement has the effect that the advancing boundary 52 of an electrolyte-deficient region 54 will reach the secondary reference element 8 before the primary reference element 6.

As a preferred choice, the electrolyte 10, the primary electrolyte 24, and the secondary electrolyte 44 contain a suspension of micro-particulate potassium chloride in an aqueous solution of potassium chloride. The proportion of suspended potassium chloride should be at least 30% and may be as high as 1500% in relation to the dry weight of the polymer substance. A preferred range is between 100% and 800%, with 200% to 400% being most preferred. Instead of an aqueous solution, it is also possible to use a part-aqueous solution of potassium chloride, for example a solution of potassium chloride in a mixture of water and glycerin or ethylene glycol. This has the effect of reducing the partial vapor pressure of the water, which is desirable especially in applications at elevated temperatures. Alternatively, the electrolyte 10 and/or the primary electrolyte 24 and/or the secondary electrolyte 44 could form a solid-phase electrolyte together with the polymer substance.

As the state of aging of the measuring probe progresses with the increase in accumulated operating time, an increasing portion of the electrolyte 10, i.e., of the potassium- and chloride ions initially contained in the filler mass 16, migrates into the sample solution. As a consequence, the enclosed space 4 will be divided into an electrolyte-deficient region 54 in which all suspended KCl particles have been dissolved and a non-deficient region 56 where the KCl has not yet been used up. The boundary zone 52 that separates the regions 54 and 56 advances over time from the opening 12 towards the interior of the measuring probe.

Instead of a suspension of KCl particles, one could also use a near-saturated solution of, e.g., approximately 3-molar concentration of potassium chloride in water. However, this has the disadvantage that the measuring probe will have a shorter operating time, because the initial amount of potassium chloride distributed in the filler mass 16 will be smaller than with an electrolyte suspension.

In the example of FIG. 1, the boundary 52 of the electrolyte deficiency advances essentially along the lengthwise axis A of the housing 2. After the boundary 52 has reached and already passed the open end 38 of the secondary reference element 8, as illustrated in FIG. 1, the interior of the secondary reference element 8 will become deficient in secondary electrolyte 44. This will cause a change in the previously constant potential $V_2$ of the secondary electrode 40. With a continued use of the measuring probe, the boundary 52 would advance to the primary reference element 6, where it would cause a change of the potential $V_1$ of the primary electrode 20.

In using the measuring probe, the primary reference element is employed in a manner that is known per se to perform a prescribed potentiometric measurement, e.g., in a process-monitoring or process-control application. With the staggered arrangement of the reference elements, there will be a delay interval from the time when the electrolyte deficiency causes a change in the potential of the secondary electrode 40 until an unwanted change occurs in the potential of the primary electrode 20. Therefore, the first occurrence of a change in the potential difference $V_1-V_2$ can be used as an advance warning of an unwanted change in the potential $V_1$ of the primary electrode 20. The time delay depends on the lengthwise offset L by which the reference elements are staggered in relation to each other and on the speed at which the boundary 52 advances. The speed of advancement, in turn, depends on the material properties of the filler mass 16 and also on the operating conditions of the measuring probe. For a given kind of application, the time delay can be determined directly from trial experiments. If the primary electrode 20 and the secondary electrode 40 are substantially identical, the difference $V_1-V_2$ of the electrode potentials will be essentially zero in the initial state, i.e., before the electrolyte becomes deficient.

In monitoring the state of aging of the measuring probe, it is practical to compare the difference $V_1-V_2$ of the electrode potentials to a prescribed warning threshold, either continuously or at certain time intervals. In addition or as an alternative, the rate of change of the difference $V_1-V_2$ of the electrode potentials can be compared against a prescribed threshold rate. If a threshold has been found to be exceeded, this will serve as a signal that appropriate measures must be taken either immediately or after a prescribed additional operating time span. For example, the measuring probe will have to be replaced, or its filler mass will have to be regenerated.

Figure 2:
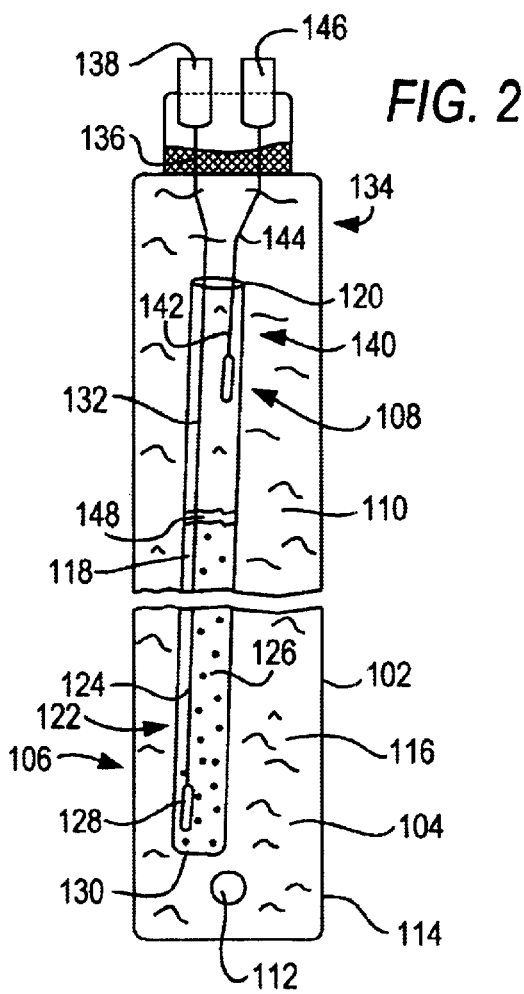
FIG. 2 represents a lengthwise section of a measuring probe (shortened by cutting out the mid-section in the drawing) in which the migration path for the boundary of the electrolyte-deficient region has been made longer.

FIG. 2 illustrates a measuring probe with a significantly lengthened path of advancement of the boundary zone. The measuring probe has a tubular housing 102 of an electrically insulating material, for example glass or a polymer material such as a polyarylether ketone (PAEK), in particular a polyether-ether ketone (PEEK). An enclosed space 104 in the housing 102 contains a primary reference element 106, a secondary reference element 108, as well as an electrolyte 110. An end portion 114 of the housing 102 has an opening 112. The enclosed space 104 is filled with an ion-permeable, high-viscosity, micro-porous polymer substance that forms a filler mass 116 together with the electrolyte 110. Preferably, the filler mass 116 is of the same composition as in the example of FIG. 1.

As illustrated in FIG. 2, the primary reference element 106 is configured as a cartridge with a tube 118 that runs essentially parallel to the housing 102 and is open at one end, oriented so that the open end 120 of the cartridge tube 118 faces in the opposite direction from the opening 112 of the measuring probe housing 102. The primary reference element contains a primary electrode 122 with a known electrode potential. In the illustrated example, the primary electrode is an Ag/AgCl electrode with a silver wire 124 that is chlorided at the end and immersed in a primary electrolyte 126. To prevent the primary electrolyte 126 from running out of the open end 120 of the cartridge tube 118, the electrolyte is enclosed in the pores of an ion-permeable, micro-porous polymer substance, preferably the same as in the filler mass 116. The chlorided end portion 128 of the silver wire 124 is arranged advantageously in the proximity of the closed end 130 of the cartridge tube 124. A wire lead 132, e.g. a platinum wire, connects the silver wire 124 to an external plug-in contact 138 by way of a seal 136, for example a glass or plastic seal, in the header part 134 of the housing 102.

The secondary reference element 108 is arranged near the open end of the cartridge tube 118 and has a secondary electrode 140 with a silver wire 142 that is chlorided at its end portion. The chlorided silver wire is immersed in a part of the primary electrolyte 126 that is near the open end 120 of the cartridge tube 118. Thus, the primary electrolyte in this case also serves as secondary electrolyte. The secondary electrode 140 is connected to an external plug-in contact 146 by a wire lead 144 running through the seal 136 in the header part 134 of the housing 102.

In the example of FIG. 2, the electrolyte-deficient region advances from the opening 112 along a path that leads first to the open end of the cartridge tube 118, then turns into the downward direction and continues all the way through the cartridge tube into the area near the closed end 130. FIG. 2 illustrates a situation where the boundary 148 of the electrolyte-deficient portion has already progressed into the interior of the cartridge tube 118.

Figure 3:
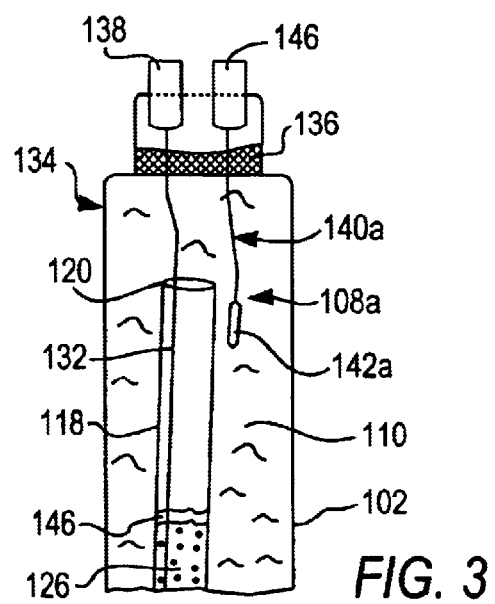
FIG. 3 represents a lengthwise section of the upper part of another measuring probe in which the migration path for the boundary of the electrolyte-deficient region has been made longer.

As an alternative to the arrangement of FIG. 2, FIG. 3 illustrates a configuration where the secondary electrode 140a is arranged outside of the cartridge tube 118. Preferably, the silver wire 142a with the chlorided end portion is immersed in a part of the electrolyte 110 immediately outside the open end 120 of the cartridge tube 118.

In place of the wire electrodes shown in the drawing figures, one could use electrodes in the form of conductive tracks, a concept that is known per se. In any one of the foregoing embodiments, such tracks could be deposited on the inner or outer wall surface of a reference-element cartridge or on the inside wall surface of the probe housing.

In addition to the foregoing embodiments, which are designed for the measurement of ion concentrations or redox potentials, it is also possible to incorporate the inventive measuring probe in a single-rod measuring chain. In this case, a measuring electrode, e.g., a pH electrode, needs to be added to the measuring probe. As a preferred configuration, the measuring electrode is arranged as a central tube running lengthwise inside a ring-shaped reference electrode as shown, e.g., in FIG. 4 of DE 34 05 431 C2.

LIST OF REFERENCE NUMBERS

2 Housing
4 Enclosed space in 2
6 Primary reference element
8 Secondary reference element
10 Electrolyte
12 Opening in 2
14 End portion of 2
16 Filler mass
18 Cartridge of 6
20 Primary electrode
22 Chlorided silver wire of 20
24 Primary electrolyte
26 Open end of 18
28 Conductor lead for 20
30 Plug-in contact for 28
32 Header of 2
34 Sealing plug of 18
36 Cartridge of 8
38 Open end of 36
40 Secondary electrode
42 Chlorided silver wire of 40
44 Secondary electrolyte
46 Conductor lead for 40
48 Plug-in contact for 46
50 Sealing plug of 36
52 Boundary of electrolyte-deficient region
54 Electrolyte-deficient region of 16
56 Non-deficient region of 16
102 Housing
104 Enclosed space of 102
106 Primary reference element
108, 108a Secondary reference element
110 Electrolyte
112 Opening of 102
114 End portion of 102
116 Filler mass
118 Cartridge tube
120 Open end of 118
122 Primary electrode
124 Chlorided silver wire of 122
126 Primary electrolyte
128 Chlorided end portion of 124
130 Closed end of 118
132 Conductor lead for 122

134 Header of 102
136 Seal of 102
138 Plug-in contact of 132
140, 140a Secondary electrode
142, 142a Chlorided silver wire of 140
144 Conductor lead for 140
146 Plug-in contact for 144
148 Boundary of electrolyte-deficient region
A Longitudinal axis of 2
$V_1$ Potential of the primary electrode
$V_2$ Potential of the secondary electrode

What is claimed is:

1. A measuring probe for potentiometric measurements, comprising:

a housing of an electrically insulating material surrounding an enclosed space;

contained inside the enclosed space, a primary reference element, a secondary reference element, an electrolyte, and an ion-permeable, micro-porous, high-viscosity polymer substance which, in combination with the electrolyte, forms a filler mass of the measuring probe;

wherein the housing has at least one opening through which the electrolyte can be brought into contact with a solution on which a measurement is to be performed, wherein the primary reference element comprises a primary electrode and the secondary reference element comprises a secondary electrode, each electrode being configured as a wire electrode in the form of a silver wire having one end coated with silver chloride, the primary electrode being directly immersed in a primary electrolyte and the secondary electrode being directly immersed in a secondary electrolyte, and wherein the secondary reference element is arranged in such a manner that an electrolyte deficiency advancing over time from the at least one opening towards the primary reference element arrives at the secondary reference element before reaching the primary reference element.

2. The measuring probe of claim 1, wherein the primary reference element comprises a primary cartridge containing the primary electrode and the primary electrolyte.

3. The measuring probe of claim 2, wherein the primary cartridge has a primary passage opening.

4. The measuring probe of claim 2, wherein the primary cartridge comprises a primary polymer substance mixed with the primary electrolyte, and said primary polymer substance is of the same kind as the polymer substance in the filler mass.

5. The measuring probe of claim 2, wherein the secondary electrode has one end immersed in the primary electrolyte.

6. The measuring probe of claim 2, wherein the secondary electrode has one end immersed in the electrolyte at a location outside of the primary cartridge.

7. The measuring probe of claim 1, wherein the secondary reference element comprises a secondary cartridge containing the secondary electrode and the secondary electrolyte.

8. The measuring probe of claim 7, wherein the secondary cartridge has a secondary passage opening.

9. The measuring probe of claim 7, wherein the secondary cartridge comprises a secondary polymer substance mixed with the secondary electrolyte, and said secondary polymer substance is of the same kind as the polymer substance in the filler mass.

10. The measuring probe of claim 1, wherein the electrolyte comprises a suspension of homogeneously distributed particles of a neutral salt with ions of equal transport number in a solution of the neutral salt.

11. The measuring probe of claim 10, wherein the neutral salt comprises potassium chloride.

12. The measuring probe of claim 11, wherein the solution comprises an at least part-aqueous potassium chloride solution and the distributed particles comprise a weight portion equal to at least 30% of a dry weight of the polymer substance.

13. The measuring probe of claim 12, wherein said weight portion is between 30% and 1500%.

14. The measuring probe of claim 13, wherein said weight portion is between 100% and 800%.

15. The measuring probe of claim 14, wherein said weight portion is between 200% and 400%.

16. The measuring probe of claim 1, wherein the measuring probe is designed as a reference electrode.

17. The measuring probe of claim 16, wherein the measuring probe is designed to be part of a single-rod measuring chain.

18. The measuring probe of claim 1, further comprising means for monitoring a difference between an electrical potential $V_1$ of the primary reference element and an electrical potential $V_2$ of the secondary reference element.

19. A method of monitoring a state of aging of the measuring probe of claim 1, comprising the steps of:

a) detecting a difference $(V_1-V_2)$ between an electrical potential $V_1$ of the primary reference element and an electrical potential $V_2$ of the secondary reference element, said detection being performed in one of a continuous mode and an intermittent mode; and b) generating an indication when the difference $(V_1-V_2)$ exceeds a previously specified threshold value.

20. A method of monitoring a state of aging of the measuring probe of claim 1, comprising the steps of:

a) detecting a difference $(V_1-V_2)$ between an electrical potential $V_1$ of the primary reference element and an electrical potential $V_2$ of the secondary reference element, said detection being performed in one of a continuous mode and an intermittent mode;

b) determining a rate of change of said difference $(V_1-V_2)$; and c) generating an indication when the rate of change exceeds a previously specified threshold rate.

21. The measuring probe of claim 1, wherein the primary reference element and the secondary reference element are essentially identical.

22. A measuring probe for potentiometric measurements, comprising:

a housing of an electrically insulating material surrounding an enclosed space;

contained inside the enclosed space, a primary reference element, a secondary reference element, an electrolyte, and an ion-permeable, micro-porous, high-viscosity polymer substance which, in combination with the electrolyte, forms a filler mass of the measuring probe;

wherein the housing has at least one opening through which the electrolyte can be brought into contact with a solution on which a measurement is to be performed, and wherein at least one of the primary and secondary reference elements comprises an electrode formed as a conductive track on a carrier surface, and wherein the secondary reference element is arranged in such a manner that an electrolyte deficiency advancing over time from the at least one opening towards the primary reference element arrives at the secondary reference element before reaching the primary reference element.

* * * * *